(12) United States Patent
Leflaive et al.

(10) Patent No.: US 7,915,471 B2
(45) Date of Patent: Mar. 29, 2011

(54) METHOD FOR PRODUCING PARAXYLENE COMPRISING AN ADSORTION STEP AND TWO ISOMERIZATION STEPS

(75) Inventors: Philibert Leflaive, Bures sur Yvette (FR); Luc Wolff, Lyons (FR); Gérard Hotier, Rueil Malmaison (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 917 days.

(21) Appl. No.: 10/580,345

(22) PCT Filed: Nov. 23, 2004

(86) PCT No.: PCT/FR2004/002984
§ 371 (c)(1),
(2), (4) Date: May 21, 2007

(87) PCT Pub. No.: WO2005/054161
PCT Pub. Date: Jun. 16, 2005

(65) Prior Publication Data
US 2008/0262282 A1 Oct. 23, 2008

(30) Foreign Application Priority Data
Nov. 26, 2003 (FR) ..................... 03 13964

(51) Int. Cl.
*C07C 7/12* (2006.01)
(52) U.S. Cl. .................. 585/828; 585/820; 585/477
(58) Field of Classification Search .......... None
See application file for complete search history.

(56) References Cited

U.S. PATENT DOCUMENTS

| | | | |
|---|---|---|---|
| 5,629,467 A | 5/1997 | Hotier et al. | |
| 5,922,924 A | 7/1999 | Hotier et al. | |
| 6,147,272 A * | 11/2000 | Mikitenko et al. | 585/812 |
| 6,359,186 B1 | 3/2002 | Hotier et al. | |
| 6,376,734 B1 * | 4/2002 | Magne-Drisch et al. | 585/805 |
| 6,448,457 B1 | 9/2002 | Hesse et al. | |
| 6,706,938 B2 * | 3/2004 | Roeseler et al. | 585/820 |
| 7,592,499 B2 * | 9/2009 | Wolff et al. | 585/805 |
| 2002/0103408 A1 * | 8/2002 | Roeseler et al. | 585/820 |
| 2002/0143223 A1 * | 10/2002 | Leflaive et al. | 585/820 |
| 2005/0038308 A1 * | 2/2005 | Wolff et al. | 585/805 |

FOREIGN PATENT DOCUMENTS

| | | |
|---|---|---|
| EP | 0531191 | 3/1993 |
| FR | 2782714 | 3/2000 |
| FR | 2792632 | 10/2000 |

* cited by examiner

*Primary Examiner* — Tam M Nguyen
(74) *Attorney, Agent, or Firm* — Millen, White, Zelano & Branigan, P.C.

(57) ABSTRACT

A process for producing para-xylene from a hydrocarbon feed is described in which an adsorption column operating as a simulated moving bed with at least five zones delivers an extract, a 2-raffinate and an intermediate raffinate.

The extract is distilled and the distillate is optionally re-crystallized to recover para-xylene with a purity of at least 99.7%. The 2-raffinate is distilled then isomerized in a reactor preferably operating in the liquid phase and at a low temperature. The intermediate raffinate with an enriched ethylbenzene content is distilled then isomerized in the vapour phase.

17 Claims, 2 Drawing Sheets

FIG.1

METHOD FOR PRODUCING PARAXYLENE COMPRISING AN ADSORTION STEP AND TWO ISOMERIZATION STEPS

FIELD OF THE INVENTION

Para-xylene production has been increasing steadily for thirty years at a mean annual rate of 5% to 6%. Para-xylene is used to produce terephthalic acid and polyethylene terephthalate resins for synthetic textiles, audio and video cassettes, bottles and, more generally, plastic materials.

To satisfy the ever-increasing demand for para-xylene, petrochemists can choose between increasing the capacity of existing units or constructing new units, which will necessarily be larger as the break-even point for such units is about 400000 tonnes/year.

The present invention can satisfy these two cases and accommodate an increase in the capacity of existing units (usually termed debottlenecking) as the modifications involved are relatively modest.

All of the equipment in an existing production unit may be re-used, the additions consisting of 1) one on-off valve per bed or a modified rotary valve in the adsorption section of the simulated moving bed separation unit; 2) a column for distilling the 2-raffinate in the distillation section of said unit; 3) an isomerization reactor, preferably in the liquid phase; 4) a para-xylene recrystallization unit.

These additions allow the para-xylene production to be increased by about thirty percent compared with an existing unit at a low cost and without increasing the unit operating cost.

DISCUSSION OF THE PRIOR ART

The production of high purity para-xylene using separation by adsorption is well known in the art. The prior art describing the production of very high purity para-xylene is illustrated in the Applicant's European patent EP-A-0 531 191.

The production of para-xylene with a purity of the order of 90-95% by simulated moving bed adsorption followed by a final purification to more than 99.7% by crystallization is also well known in the art. This is illustrated by the Applicant's U.S. Pat. No. 5,922,924 and U.S. Pat. No. 5,948,950.

These patents disclose the design (types of zeolite, number of beds, distribution per zone of beds) and operation (definition of 3 ratios: solvent to feed, recycle to feed, extract to raffinate) of the adsorption unit to increase the productivity of the zeolite, reduce the number of beds from 24 to between 8 and 15 depending on the case, and to reduce the solvent to feed ratio by loosening the purity requirements.

The Applicant's French patent FR-A-2 792 632 teaches that it is possible to use two distinct isomerization units in the loop processing aromatic compounds containing 8 carbon atoms.

The flowchart described in that patent uses a distillation column, termed the ethylbenzene separation column, which may have up to 200 plates and must be operated at a very high recycle ratio. A first stream is extracted overhead from said distillation column, which stream is a fraction which is rich in ethylbenzene which is isomerized in the vapour phase under the following conditions: a temperature of more than 300° C., preferably 360° C. to 480° C., a pressure of less than 2.5 MPa, preferably 0.5 to 0.8 MPa (1 MPa=$10^6$ Pascals), an hourly space velocity of less than 10 $h^{-1}$, preferably in the range 0.5 to 6 $h^{-1}$, and a molar ratio of hydrogen to hydrocarbon of less than 10, preferably in the range 3 to 6.

Liquid phase isomerization can be carried out under the following conditions: a temperature of less than 300° C., preferably in the range 200° C. to 260° C., a pressure of less than 4 MPa, preferably in the range 2 to 3 MPa, an hourly space velocity of less than 10 $h^{-1}$, preferably in the range 2 to 4 $h^{-1}$, with a catalyst based on ZSM-5 zeolite, for example.

The advantages of operating with two distinct isomerization steps are twofold:
   low temperature liquid phase isomerization minimizes unwanted cracking, transalkylation and disproportionation reactions but limits ethylbenzene conversion;
   high temperature vapour phase isomerization with a feed which is rich in ethylbenzene encourages conversion of that product, with the thermodynamic equilibrium at about 8%.

However, the disadvantage of the process described in FR-A-2 792 632 resides in the fact that the distillation column for separating the two streams is very expensive both to install and to operate.

The present invention can directly obtain the two streams each supplying an isomerization unit by withdrawing two distinct raffinates from the adsorption column, one termed the intermediate raffinate which will supply a first vapour phase isomerization step after eliminating the desorbant, the other termed the 2-raffinate, which will supply a second isomerization step, preferably in the liquid phase, after eliminating the desorbant.

Thus, the present invention retains the advantages of using two distinct isomerization steps by carrying out these isomerizations on two raffinates, which overcomes the disadvantage of a very expensive distillation column.

Several prior art documents describe the extraction of two raffinates with distinct compositions from a simulated moving bed adsorption column.

U.S. Pat. No. 4,313,015 describes such a simulated moving bed separation over X zeolite exchanged with barium, the desorbant being diethylbenzene.

The extract obtained is constituted by para-xylene which is not pure enough (99.44%) to reach current standards (currently 99.7% minimum) and in a yield of 97.5%.

Other documents (FR-A-2 782 714, FR-A-2 808 270, FR-A-2 822 820, FR-A-2 829 758 and FR-A-2 833 592 from the Applicant) also illustrate separations using a simulated moving bed column from which two distinct raffinates are extracted in addition to the extract. They are all aimed at co-producing commercial purity para-xylene, meta-xylene and/or ortho-xylene.

Those documents describe the withdrawal of two distinct raffinates from a simulated moving bed adsorption column, but have limitations either as regards the purity of the para-xylene obtained, or as regards the yield of para-xylene, linked to the co-production of other isomers.

BRIEF DESCRIPTION OF THE INVENTION

The main aim of the invention is to obtain para-xylene with a purity of at least 99.7%. The process of the invention is a process for producing para-xylene from a feed containing xylenes, ethylbenzene and C9+ hydrocarbons, comprising at least the following steps:
   a step for adsorption in a unit operating as a simulated moving bed from which at least three effluents are produced: an extract essentially constituted (i.e. at least 50% by weight) by para-xylene and desorbant; an intermediate fraction termed the intermediate raffinate, which essentially contains ethylbenzene, preferably in a high yield; and a second fraction, termed the 2-raffinate, which essentially contains a mixture of meta- and ortho-xylene, preferably substantially free of para-xylene and with an ethylbenzene content which is preferably less than 5%;

a step for isomerization of C8 aromatics, in a unit operating in the vapour phase and converting ethylbenzene, to treat the intermediate raffinate;

a step for isomerization of C8 aromatics in a unit operating in the liquid phase or in the vapour phase, preferably in the liquid phase, to treat the 2-raffinate.

Depending on the adjustment of the simulated moving bed adsorption unit, the extract may be constituted by para-xylene with a purity which is sufficient to be commercial (i.e. more than 99.7%) and desorbant, or it may be constituted by para-xylene with an insufficient purity. In this last case, the extract, previously freed of desorbant by distillation, is preferably purified by crystallization.

Said crystallization is preferably carried out between +10° C. and −30° C. as described, for example, in EP-B1-0 531 191. The mother liquor from the crystallization step may then be recycled to the supply to the simulated moving bed adsorption unit.

The solvent for washing the para-xylene crystals is, for example, selected from the following solvents: n-pentane, water, purified para-xylene or toluene, and the mother liquor from washing in the washing step may be recycled to the supply to the simulated moving bed adsorption column.

More particularly, when debottlenecking an existing unit, the invention preferably comprises, in combination:

an adsorption step in a unit operating as a simulated moving bed which comprises three effluents: a) an extract constituted by desorbant and para-xylene the purity of which is preferably of the order of 90-95% as a percentage by weight; b) an intermediate raffinate which contains ethylbenzene, preferably in a high yield; and c) a 2-raffinate which contains a mixture of meta- and ortho-xylene substantially free of para-xylene, typically less than 1%, and with an ethylbenzene content which is preferably less than 5%;

a step for purification of para-xylene by crystallization of at least a portion of the extract;

a step for isomerizing C8 aromatics, in a unit operating in the vapour phase at high temperature and converting ethylbenzene to treat the intermediate raffinate;

a step for isomerizing C8 aromatics in a unit preferably operating in the liquid phase, to treat the 2-raffinate.

DETAILED DESCRIPTION OF THE INVENTION

Figure 1:
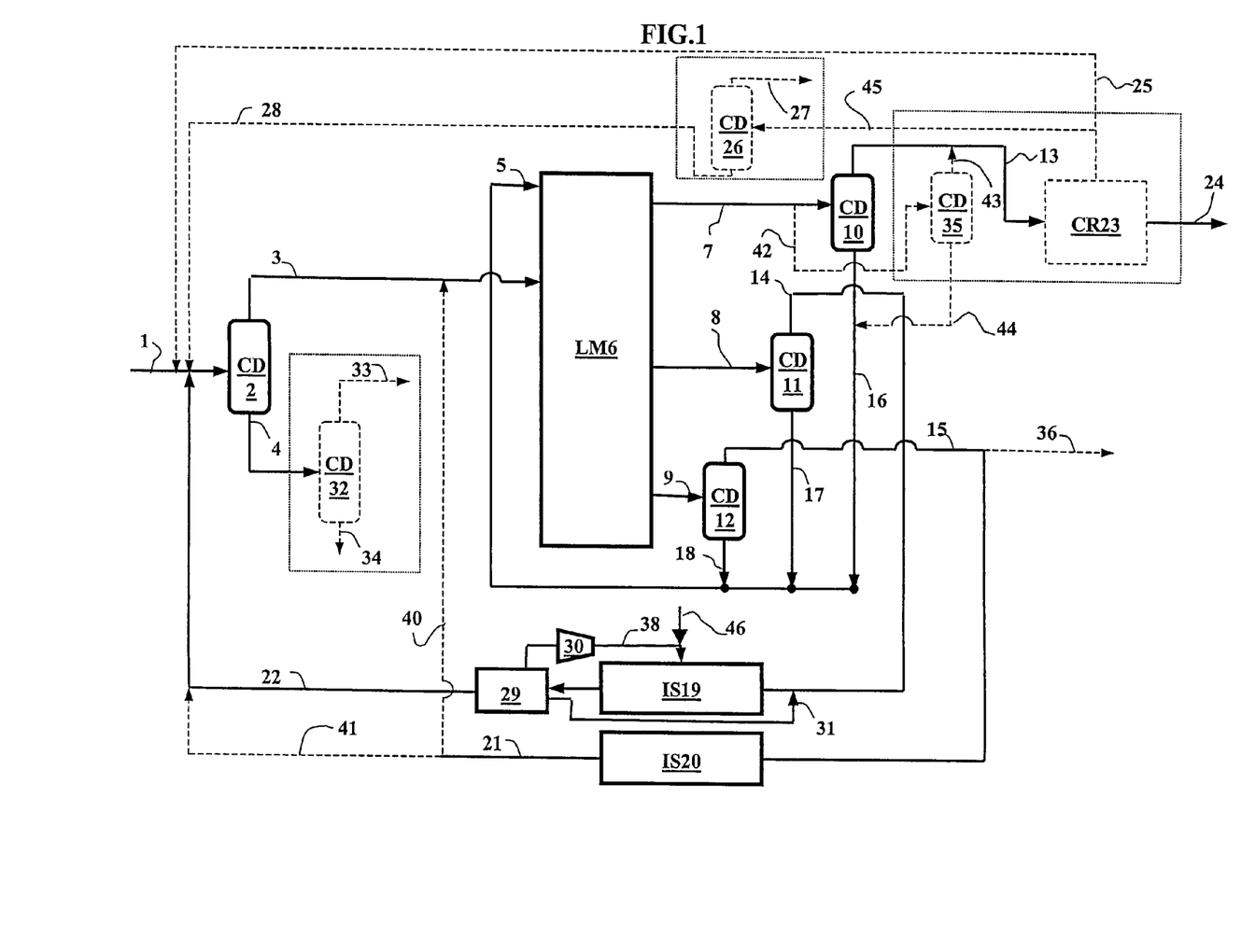
FIG. 1 shows a flowchart of the process of the invention. The parts shown as dotted lines correspond to optional variations.

In a preferred implementation, the process for producing para-xylene of the invention from a feed containing xylenes, ethylbenzene and C9+ hydrocarbons comprises at least the following steps (FIG. 1):

sending the feed (1) to a distillation column (CD2) from which a mixture (3) is extracted overhead comprising most of the meta-xylene, para-xylene, ethylbenzene and at least a portion of the ortho-xylene, and from which a stream (4) of C9-C10 hydrocarbons and the remaining portion of the ortho-xylene are extracted from the bottom;

separating the overhead mixture (3) in a simulated moving bed in at least one separation column (LM6) containing a plurality of interconnected beds and operating as a closed loop, said column comprising at least five zones defined by the injections of the stream (3) constituting the feed for the column (LM6) and the desorbant (5) and the withdrawals of an extract (7) containing para-xylene, an intermediate raffinate (8) containing ethylbenzene and a 2-raffinate (9) containing ortho-xylene and meta-xylene, the para-xylene desorption zone 1 being included between the desorbant injection (5) and the extract removal (7); the ethylbenzene, ortho-xylene and meta-xylene desorption zone being included between the extract removal zone (7) and the adsorption feed injection (3); the para-xylene adsorption zone 3A being included between the feed injection (3) and the intermediate raffinate withdrawal (8); the ethylbenzene adsorption zone 3B being included between the intermediate fraction withdrawal (8) and the 2-raffinate withdrawal (9); and the zone 5 being included between the 2-raffinate withdrawal (9) and the desorbant injection (5);

distilling the intermediate raffinate (8) in a column (CD11) to eliminate substantially all of the desorbant and withdrawing a first distilled fraction (14) containing ethylbenzene;

distilling the 2-raffinate in a column (CD12) to eliminate substantially all of the desorbant and withdrawing a second distilled fraction (15); distilling the extract (7) in a column (CD10) to recover a fraction (13) which is enriched in para-xylene;

sending said first distilled fraction (14) to a first zone for isomerizing C8 aromatics (IS19) operating in the vapour phase and converting ethylbenzene to obtain a first isomerate (22);

sending at least a portion of said second distilled fraction (15) to a second xylene isomerization zone (IS20) to obtain a second isomerate (21);

sending the first isomerate (22), after eliminating its light fractions, into a separation train (29) towards the distillation column (CD2);

recycling the second isomerate (21) either (stream 40) to the simulated moving bed separation column (LM6) as a mixture with the overhead stream (3) from the distillation column (CD2) or (stream 41) to the distillation column (CD2) as a mixture with the feed (1).

In a more preferred variation of the invention, the fraction (13) from the extract (7) is enriched in para-xylene with a purity of at least 50%, and is sent to at least one crystallization zone (CR23) to deliver para-xylene crystals and a mother liquor, the crystals being separated from the mother liquor, optionally taken up in suspension, washed and recovered (stream 24) and the mother liquor (25) is mixed with the feed (1) supplying the simulated moving bed separation column (LM6) via the column (CD2).

The first isomerization zone (IS19) operating in the gas phase is generally operated under the following conditions:

a temperature of more than 300° C., preferably 350° C. to 480° C.;

a pressure of less than 4 MPa, preferably 0.5 to 2 MPa;

an hourly space velocity (HSV) of less than $10 h^{-1}$ (10 litres per litre per hour), preferably in the range 0.5 to 6 $h^{-1}$;

a catalyst containing a zeolite with structure type EUO, and at least one group VIII metal;

a $H_2$/hydrocarbon molar ratio of less than 10, preferably in the range 3 to 6.

The second isomerization zone (IS20) preferably operates in the liquid phase and is operated under the following conditions:
- a temperature of less than 300° C., preferably 200° C. to 260° C.;
- a pressure of less than 4 MPa, preferably 2 to 3 MPa;
- an hourly space velocity (HSV) of less than 10 $h^{-1}$, preferably in the range 2 to 4 $h^{-1}$;
- a catalyst containing a ZSM-5 type zeolite.

It is optionally possible to operate said second isomerization zone with a makeup of hydrogen, so that, for example, the $H_2$/hydrocarbon molar ratio is less than 10, preferably in the range 3 to 6. Such an operation with hydrogen makeup is particularly preferred when said second isomerization zone is operated in the vapour phase.

In a further variation of the process of the invention, the stream (4) from the bottom of the distillation column (CD2) is distilled in a distillation column (CD32) to produce an overhead stream (3) of high purity ortho-xylene, and a bottom stream (34) containing C9-C10 hydrocarbons. In a sub-variation of the preceding variation, the stream containing ortho-xylene (33) is recycled to the liquid phase isomerization zone (IS20).

The adsorbent used in the simulated moving bed separation unit (LM6) is generally a barium-enriched X zeolite or a potassium-enriched Y zeolite or a barium and potassium-enriched Y zeolite.

The desorbant used in the simulated moving bed separation unit (LM6) is generally selected from para-diethylbenzene, toluene, para-difluorobenzene or a mixture of diethylbenzenes. The volume ratio of the desorbant to the feed in the simulated moving bed separation unit (LM6) is in the range 0.5 to 2.5, preferably in the range 1.4 to 1.7.

The simulated moving bed separation unit (LM6) is operated at a temperature in the range 20° C. to 250° C., preferably in the range 90° C. to 210° C., and more preferably in the range 160° C. to 200° C., and at a pressure in the range from the bubble point of xylenes at the operating temperature to 2 MPa. The ethylbenzene content of the second distilled fraction from the 2-raffinate (stream 15) is at most 5% by weight, and is preferably less than 1% by weight.

The gas phase isomerization unit (IS19) may comprise a zeolite with structure type EUO, and at least one metal from group VIII of the periodic table in a proportion of 0.01% to 2% by weight with respect to the catalyst. The catalyst for the gas phase isomerization unit (IS19) may in some cases contain an EU-1 zeolite and platinum.

In a variation of the invention, a portion of the distilled stream from the 2-raffinate (stream 15) may be sent to a set of units which can produce high purity meta-xylene and/or ortho-xylene.

The process of the invention is particularly suited to modification of an existing unit to increase the quantity of para-xylene produced.

The function of the process of the invention, in particular the composition of the various streams, is set out below with reference to FIG. 1. The fresh feed is introduced via line (1) into a distillation column (CD2). This fresh feed contains mainly C8 aromatics, xylenes and ethylbenzene in varying proportions depending on the origin of the cut. It may possibly contain impurities in a varying quantity depending on the origin of the feed, which will essentially be C9 and C10 aromatic compounds and paraffinic and naphthenic compounds.

The amount of naphthenic or paraffinic impurities is advantageously less than 1% by weight. Preferably, this amount is less than 0.3% by weight and more preferably, this amount is less than 0.1% by weight. The feed may derive either from an aromatization unit or from a toluene disproportionation unit or from a unit for transalkylation of toluene and C9 aromatics.

An isomerate supplied via a line (22) is added to the fresh feed, optionally along with a mother liquor via lines (25) or (28) with a para-xylene content which is advantageously in the range 25% to 40%. The streams (1), (22) and (28) or (25) supply a distillation column (CD2).

The effluent (4) from the bottom of the column (CD2) is essentially constituted by C9 and C10 aromatic compounds and possibly by ortho-xylene. Optionally, the mixture (4) of ortho-xylene and C9-C10 aromatic hydrocarbons withdrawn from the bottom of the distillation column (CD2) may be sent to another distillation column (CD32) from which an overhead stream (33) of high purity ortho-xylene (at least 98.5%) is extracted along with a bottom stream (34) containing C9-C10 hydrocarbons.

The overhead effluent (3) from the column (CD2) as well as the optional isomerate moving in line (21) constitute the feed for a simulated moving bed separation unit (LM6). The simulated moving bed separation unit (LM6) is supplied by the feed moving in line (3) and by the desorbant moving via a line (5).

Any type of desorbant may be used. The preferred desorbant is para-diethylbenzene, but other desorbants such as toluene, para-difluorobenzene or a mixture of diethylbenzenes may also be suitable.

The effluents from the unit (LM6) are an extract (7), an intermediate raffinate (8) and a 2-raffinate (9), said separation unit comprising at least five zones defined by the feed and desorbant injections and the withdrawals of intermediate raffinate, 2-raffinate and extract:
- the para-xylene desorption zone 1, included between the desorbant injection (5) and the extract removal point (7), preferably comprises at least 4 beds of adsorbent;
- the ethylbenzene, ortho-xylene and meta-xylene desorption zone 2, included between the extract removal zone (7) and the feed adsorption injection (3), preferably comprises at least 9 beds of adsorbent;
- the para-xylene adsorption zone 3A, included between the feed injection (3) and the intermediate raffinate withdrawal (8), preferably comprises at least 4 beds of adsorbent;
- the ethylbenzene adsorption zone 3B, included between the intermediate fraction withdrawal (8) and the 2-raffinate withdrawal (9), preferably comprises at least three beds of adsorbent;
- the zone 4, included between the 2-raffinate withdrawal (9) and the desorbant injection (5), preferably comprises at least two beds of adsorbent.

According to a preferred characteristic of the invention, the desorbant may be injected into the zone 1 and the feed may be injected into the zone 3A of the column (LM6) in a desorbant to feed volume ratio of at most 1.7/1, preferably at most 1.5/1.

The extract (7) is essentially constituted by toluene, para-xylene and desorbant.

The intermediate raffinate (8) is essentially constituted by toluene, meta-xylene and ortho-xylene, ethylbenzene, para-xylene as regards the portion not recovered in the extract, and desorbant.

The 2-raffinate (9) is essentially constituted by meta-xylene and ortho-xylene and desorbant. It is substantially free of para-xylene and ethylbenzene. The extract (7) is sent to a distillation column (CD10).

The desorbant is withdrawn from the bottom of the column (CD10) via line (16) and returned to the zone 1 of the column (LM6) via line (5). A mixture of para-xylene and toluene is withdrawn via line (13) overhead from the column (CD10). In the case in which the para-xylene purity is not sufficient, the mixture is sent to a crystallization unit (CR23).

The unit (CR23) produces high purity para-xylene which is evacuated via line (24) and a mother liquor which may be returned either directly to the inlet to the distillation column (CD2) via the line (25) or optionally to a distillation column (CD26) which can extract toluene overhead via the line (27) and a mixture of xylenes which may contain 25% to 40% of para-xylene via the bottom line (28) which is directly recycled to the inlet to the distillation column (CD2).

The 2-raffinate (9) is sent to a distillation column (CD12). Desorbant is withdrawn from the column bottom (CD12) via a line (18) and returned via line (5). A mixture of meta-xylene and ortho-xylene is withdrawn overhead from column (CD12) via line (15) and sent to the isomerization unit, preferably in the liquid phase and at low temperature (IS20).

Optionally, a portion of stream (15) may be used for the production of high purity meta-xylene or ortho-xylene (stream 36) as described in French patent application 01/12777 or using any other means known to the skilled person.

The isomerization unit (IS20), preferably in the liquid phase, may operate under the following conditions:
 a temperature of less than 300° C., preferably in the range 200° C. to 260° C.;
 a pressure of less than 4 MPa, preferably in the range 2 to 3 MPa;
 an hourly space velocity (HSV) of less than 10 h$^{-1}$, preferably in the range 2 to 4 h$^{-1}$.

Any catalyst which can isomerize hydrocarbons containing 8 carbon atoms is suitable for the isomerization unit (IS20) of the present invention. Preferably, a catalyst containing a ZSM-5 type catalyst is used.

The effluent from the isomerization unit (IS20) is returned via line (21) either to the distillation column (CD2) or directly to the inlet to the separation unit (LM6) if the amount of compounds other than C8 aromatics is very low, typically of the order of 1% by weight.

The intermediate raffinate is sent via a line (8) to a distillation column (CD11). From the bottom of the column (CD11), the desorbant is returned via line (17) and re-introduced via line (5) to the zone 1 of the separation unit (LM6). A mixture of xylenes and ethylbenzene is withdrawn overhead from the column (CD11) via line (14). The effluents from line (14) are sent to the isomerization unit (IS19) functioning at high temperature and in the vapour phase.

The isomerization unit (IS19) is preferably operated under the following conditions:
 a temperature of more than 300° C., preferably 360° C. to 480° C.;
 a pressure of less than 2.5 MPa, preferably 0.5 to 0.8 MPa;
 an hourly space velocity of less than 10 h$^{-1}$, preferably in the range 0.5 to 6 h$^{-1}$;
 a hydrogen/hydrocarbon molar ratio of less than 10, preferably in the range 3 to 6.

Any catalyst which can isomerize hydrocarbons containing 8 carbon atoms, zeolitic or non zeolitic, is suitable for the isomerization unit (IS19) of the present invention. Preferably, a catalyst containing an acidic zeolite is used, for example with structure type MFI, MOR, MAZ, FAU and/or EUO. More preferably, a catalyst containing a zeolite with structure type EUO and at least one metal from group VIII of the periodic table is used.

Preferably, the catalyst for the isomerization unit (IS19) includes 1% to 70% by weight of a zeolite with structure type EUO (for example EU-1) comprising silicon and at least one element T preferably selected from aluminium and boron with a ratio Si/T in the range 5 to 100. Said zeolite is at least partially in the hydrogen form, and the sodium content is such that the Na/T atomic ratio is less than 0.1. Optionally, the catalyst for the isomerization unit may contain 0.01% to 2% by weight of tin or indium, and sulphur in an amount of 0.5 to 2 atoms per atom of group VIII metal.

The effluent from the isomerization unit (IS19) is sent to a separation train (29) to recover part of the hydrogen which is recycled to the isomerization unit (IS19) using a compressor (30) and line (38). The non recycled portion of the hydrogen is compensated for by a makeup of fresh hydrogen. An intermediate fraction essentially constituted by paraffinic and napthenic hydrocarbons is recovered and sent to the inlet to the isomerization unit (IS19) by means of a line (31). An isomerate recovered from the separation train (29) and constituted by the heaviest fractions is returned to the distillation column (CD2) via line (22).

In the particular case of debottlenecking of an existing aromatic loop (FIG. 2), the invention consists of increasing the flow rate of the fresh feed and the flow rate of para-xylene produced by about thirty percent while continuing to use the principal equipment of the loop, namely:
 1) the xylene distillation column (CD2);
 2) the simulated moving bed xylenes separation unit (LM6) functioning over four principal streams (desorbant, feed, extract containing high purity para-xylene, a single raffinate containing other aromatic C8 hydrocarbons);
 3) the isomerization unit (IS19) supplied via the raffinate extracted from the separation column (LM6) converting ethylbenzene using, for example, a catalyst based on a zeolite with structure type EUO comprising a reactor, a recycle compressor, a stabilization column and a column allowing C8 and C9 naphthenes to be recovered in order to recycle them to the feed.

Figure 2:
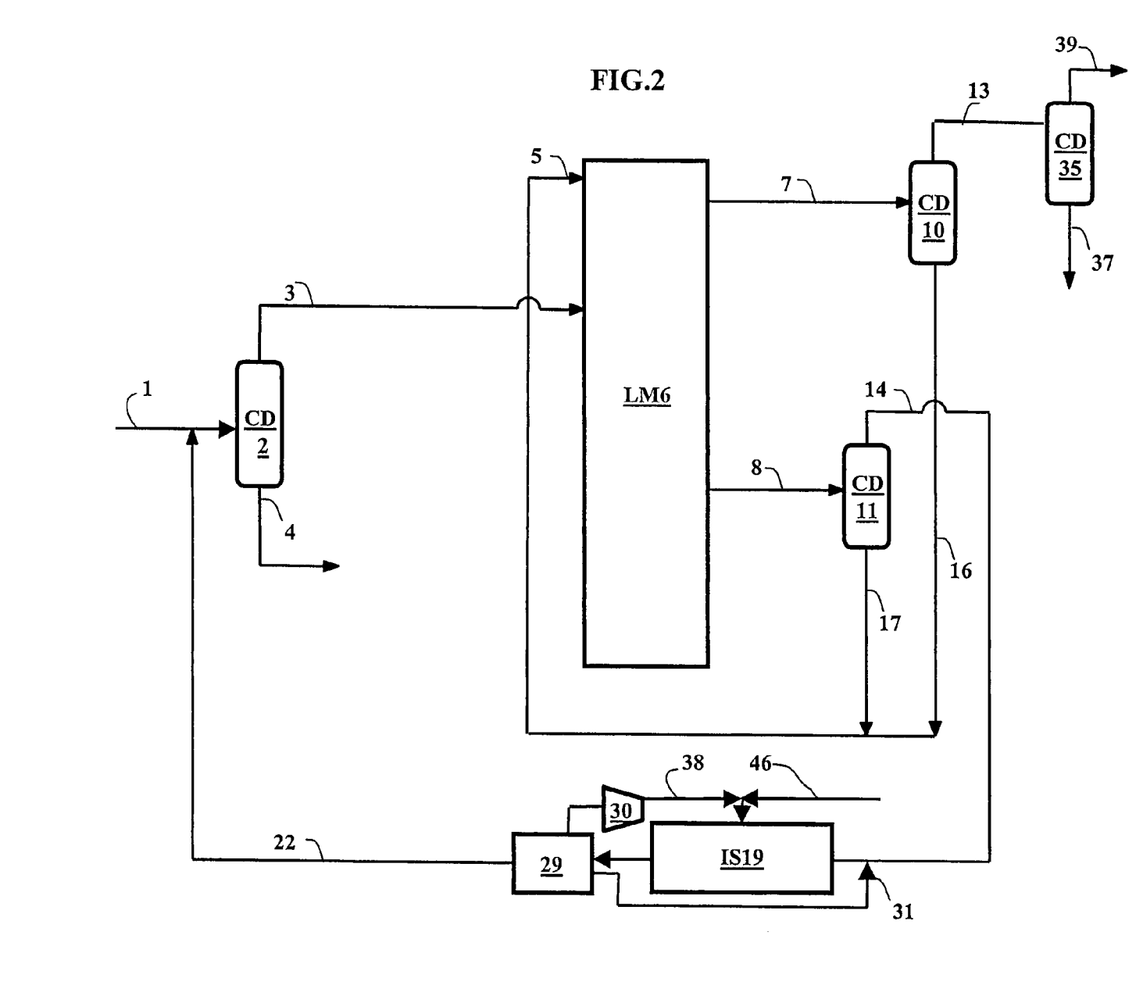
FIG. 2 shows a prior art flowchart. The stream numbers are the same as in FIGS. 1 and 2 when these streams designate similar streams in that they are streams occupying the same positions in FIG. 1 and in FIG. 2.

To carry out the debottlenecking of the invention, the simulated moving bed separation unit (LM6) will be adapted to function with five principal streams (desorbant, feed, extract, intermediate raffinate and 2-raffinate).

The conventional unit with four streams is modified to be able to integrate this fifth stream (termed 2-raffinate) and supplying a specific isomerization unit (IS20), the single raffinate before the debottlenecking then taking the name of intermediate raffinate and still supplying the isomerization unit (IS19). This modification is carried out either by adding one on-off valve per bed, the set of said valves being connected to a common collector, or by modifying the rotary valve to manage five principal streams.

In general, the mechanical strength of the distributor plates separating the beds is sufficient to accept an increase of the order of 30% in the internal flow rate. If this is not the case, the sieve will have to be discharged and the plates strengthened.

To separate the 2-raffinate from the desorbant, a new distillation column (CD12) should also be put in place. The 2-raffinate, freed of desorbant, is isomerized in the isomerization unit, preferably in the liquid phase (IS20) as described above.

It should be noted that, preferably, the isomerate obtained as the effluent from the unit (IS20) will be recycled (stream 40) directly to the adsorption unit (LM6) without passing via the xylenes column (CD2) which generally cannot accept an increase in the feed of the order of 30%.

Finally, an increase of the order of 30% in the feed flow rate and the internal traffic to the adsorption column (LM6) is obtained to the detriment of the purity of the extract.

Typically, the amount of impurities in the extract is multiplied by a factor in the range 2 to 10 depending on whether the ratio of desorbant to feed is maintained or otherwise. The result is that only units with an initial para-xylene purity of close to 99.9% could continue to produce commercializable para-xylene. In the most general case, the para-xylene purity falls below 99.6% and typically below 99%. This latter then generally undergoes final purification which is carried out in the crystallization unit (CR23).

Further, the extract column (CD10) is generally not capable of accepting an increase in the feed of the order of 30%. The solution thus consists of using the para-xylene purification column (CD35) generally existing in the aromatic loop in parallel with the extraction column (CD10).

EXAMPLES

The invention will be better understood from the following two examples: comparative Example 1 has an aromatic loop of the prior art.

Example 2 has the same loop, with an increase in capacity of 30% carried out in accordance with the invention.

Example 1

Comparative

This example illustrates the prior art and describes an aromatic loop shown in FIG. 2 and comprising:
- a xylenes column (CD2) for extracting C9 and C10 aromatics (stream 4) and sending a stream (3) essentially constituted by C8 aromatics to the adsorption unit (LM6);
- a simulated moving bed adsorption unit (LM6) with 4 zones from which an extract (7) and a single raffinate (8) are withdrawn;
- an isomerization unit (IS19) supplied by a portion (14) of the raffinate (8) after elimination of desorbant by means of the distillation column (CD11);
- a para-xylene purification column (CD35) located downstream of the distillation column (CD10). Para-xylene (stream 37) with a purity of more than 99.7% is withdrawn from the bottom of said column (CD35).

The unit employed for the flow rate was the kilotonne per year (kt/yr).

The feed (1) which supplied the aromatic loop was derived from reforming and had a flow rate of 460 kt/yr. 1540 kt/yr of isomerate (22) recycled from the isomerization unit (IS19) converting ethylbenzene was added to the feed (1). The resulting stream was distilled in the xylenes column (CD2). The operating conditions for the column were as follows:
Column: 120 plates
Head temperature: 255° C.
Head pressure: 0.95 MPa
Bottom temperature: 305° C.
Bottom pressure: 1.05 MPa.

20 kt/yr of a mixture of C9 and C10 aromatics (stream 4) was extracted from the column bottom (CD2) and 1980 kt/yr of C8 aromatics cut (stream 3) with a para-xylene content of about 21% and an ethylbenzene content of about 10% was extracted from the bottom.

This cut was sent to a simulated moving bed adsorption unit with four zones (LM6) and four principal streams: the feed (stream 3), the desorbant (stream 5), the extract (stream 7), and the raffinate (stream 8). This unit was composed of 24 beds containing a barium-exchanged X zeolite. The temperature was 175° C. The configuration was: 5 beds in zone 1, 9 beds in zone 2, 7 beds in zone 3 and 3 beds in zone 4. The desorbant was constituted by 99% para-diethylbenzene; the flow rate of desorbant (5) was 3000 kt/yr.

The flow rate of the extract (7) at the outlet from the adsorption unit (LM6) was 1200 kt/yr; it was sent to a distillation column (CD10) from the bottom of which 790 kt/yr of desorbant (16) was drawn and recycled to the adsorption unit (LM6); 410 kt/yr of a mixture (13) essentially constituted by toluene and para-xylene was withdrawn overhead.

This mixture (13) was sent to a distillation column (CD35) which could withdraw 10 kt/yr of toluene overhead and 400 kt/yr of para-xylene from the bottom (stream 37).

The para-xylene obtained was 99.8% pure. The amounts of impurities were as follows:
meta-xylene: 0.08%
ethylbenzene: 0.08%;
ortho-xylene: 0.04%.

The flow rate of the raffinate (8) was 3780 kt/yr. 2210 kt/yr of desorbant (stream 17) was withdrawn from the bottom of the column (CD11) and recycled to the separation unit (LM6); 1570 kt/yr of raffinate free of desorbant (stream 14) was withdrawn overhead from the column and had a para-xylene content of about 1%.

160 kt/yr of a C8 and C9 paraffinic and naphthenic cut (stream 31) was added to the stream (14). This mixture was injected into the isomerization reactor (IS19). 130 kt/yr of hydrogen was recycled via the compressor 30 (stream 38).

The isomerization unit (IS19) operated under the following conditions:
Temperature: 385° C.
Catalyst: contained platinum and EU-1 zeolite;
Hourly space velocity: 3.5 h$^{-1}$;
H$_2$/hydrocarbon ratio: 4.4:1
Pressure: 0.9 MPa The ethylbenzene content of the mixture introduced into the isomerization unit (IS19) was about 11.5%. At the outlet from the isomerization reactor (IS19), a separation train (29) allowed 20 kt/yr of a light gas essentially containing hydrogen, 20 kt/yr of toluene and 160 kt/yr of a paraffinic and naphthenic cut (stream 31) as cited above to be produced. The largest portion of the isomerate (stream 22), namely 1540 kt/yr, was recycled to the inlet to the xylenes column (CD2).

Example 2

In Accordance with the Invention

This example illustrates an application of the invention consisting of increasing the capacity of the aromatic loop described in Example 1 by 30%. This example is illustrated in FIG. 1 of the invention.

The simulated moving bed separation unit (LM6) is adapted to function with a new stream, termed 2-raffinate, namely to give five principal streams (desorbant, feed, extract, intermediate raffinate and 2-raffinate).

The four-stream adsorption unit (LM6) of Example 1 of the prior art was thus modified to be able to incorporate this fifth stream, either by adding one on-off valve per bed, the set of valves being connected to a common collector, or by modifying the rotary valve to manage five principal streams.

Generally, the mechanical strength of the distributor plates separating the beds is sufficient to accept an increase of the order of 30% in the internal flow rate. If this were not the case, the sieve would have to be discharged and the plates would have to be strengthened. To separate the 2-raffinate from the desorbant, a new distillation column (CD12) was also placed in position.

A crystallization unit (CR23) was also added to the aromatic loop of Example 1, supplied by the stream (13) and from which para-xylene (stream 24) was extracted, along with a mother liquor (stream 25) which was recycled to the xylenes column (CD2).

An isomerization unit (IS20) operating in the liquid phase at low temperature supplied via the stream (15), the effluent (stream 21 and 40) from which is recycled to the adsorption unit (LM6) as a mixture with the stream (3), was also added to the aromatic loop.

The simulated moving bed adsorption column (LM6) was still composed of 24 beds containing a barium-exchanged X zeolite. It now comprised 5 zones defined as follows: 5 beds in zone 1, 9 beds in zone 2, 5 beds in zone 3A, 3 beds in zone 3B and 2 beds in zone 4. The temperature was 175° C.

The liquid phase isomerization unit (IS20) operated under the following conditions:
Pressure: 2 MPa;
Temperature: 260° C.;
Catalyst: contained ZSM-5 zeolite;
Hourly space velocity: 3 $h^{-1}$.

The feed for the loop, from reforming, was 600 kt/yr, i.e. 30% more than the 460 kt/yr of Example 1. 1540 kt/yr of isomerate (stream 22), recycled from the isomerization unit (IS19) and 20 kt/yr of crystallization mother liquor (stream 28) with a para-xylene content of 38% were added to the feed (1). The resulting stream was distilled in the xylenes column (CD2).

30 kt/yr of a mixture of C9 and C10 aromatics (stream 4) was withdrawn from the bottom of the column (CD2) and 2130 kt/yr of C8 aromatic cut was withdrawn overhead (stream 3). 460 kt/yr of isomerate (stream 40) from the isomerization reactor (IS20) was added to the stream (3) and the resulting stream was sent to a simulated moving bed adsorption unit (LM6) with five zones and five principal streams. The desorbant (stream 5) was constituted by 99% para-diethylbenzene. The desorbant flow rate was 3900 kt/yr.

The flow rate of the extract (stream 7) at the outlet from the adsorption unit (LM6) was 1580 kt/yr. It was sent to the extraction (CD10) and purification (CD35) columns. The flow rate of the extract sent to the column (CD10) was 1200 kt/yr. The flow rate of the extract sent to the column (CD35) was 380 kt/yr.

1040 kt/yr of desorbant (stream 16) was withdrawn from the bottom of these columns and recycled to the simulated moving bed adsorption unit (LM6); 540 kt/yr of a mixture (stream 13) essentially constituted by toluene and para-xylene was withdrawn overhead.

This mixture (stream 13) was sent to the crystallization unit (CR23) from which 20 kt/yr of mother liquor rich in toluene (stream 25) was extracted and recycled to the inlet to the column (CD2), along with 520 kt/yr of para-xylene with a purity of 99.8% (stream 24).

The crystallization unit was constituted by two crystallization zones, the first being operated at a temperature of about 10° C., the second at a temperature of −20° C.

The flow rate of the intermediate raffinate (stream 8) was 3190 kt/yr. 1600 kt/yr of desorbant (stream 17) was withdrawn from the bottom of the intermediate raffinate distillation column (CD11) and recycled to the separation unit (LM6), and 1590 kt/yr of raffinate (stream 14) was extracted overhead with a para-xylene-content of about 1%.

160 kt/yr of a C8 and C9 paraffinic and naphthenic cut (stream 31) was added to the stream (14). The mixture of streams (14), (31) was injected as well as a recycle of 130 kt/yr of hydrogen (38), into the isomerization reactor (IS19) which operated at high temperature in the vapour phase over a catalyst containing platinum and EU-1 zeolite. The ethylbenzene content of said mixture was about 16.4%.

A separation train (29) at the outlet from the isomerization reactor (IS19) produced 25 kt/yr of a gas containing mainly hydrogen, 30 kt/yr of toluene and 160 kt/yr of the paraffinic and naphthenic cut cited above (stream 31). The largest portion of the isomerate (stream 22), namely 1540 kt/yr, was recycled to the inlet to the xylenes column (CD2). The flow rate of the 2-raffinate (stream 9) was 1720 kt/yr. 1260 kt/yr of desorbant (stream 18) was withdrawn from the bottom of the 2-raffinate distillation column (CD12) and recycled to the adsorption unit (LM6); 460 kt/yr of a stream (15) was withdrawn overhead with an ethylbenzene content of 0.07% and a para-xylene content of 0.15%.

The mixture (stream 15) was isomerized at low temperature in the liquid phase in an isomerization unit (IS20) and the isomerate obtained (stream 21) was returned directly to the inlet of the adsorption unit (LM6).

Most of the constituent elements of the initial aromatic loop were re-used, and the cost associated with a 30% increase in the production of para-xylene was substantially lower than that for a new C8 aromatic loop with the same capacity.

The invention claimed is:

1. A process for producing para-xylene from a feed containing xylenes, ethylbenzene and C9+ hydrocarbons, comprising at least the following steps:
   a step for adsorption comprising contacting said feed with an adsorbent in a unit (LM6) operating as a simulated moving bed from which at least three effluents are produced: an extract (7) essentially constituted by para-xylene and desorbant; an intermediate fraction, termed the intermediate raffinate, which essentially contains ethylbenzene, and a second fraction, termed the 2-raffinate, which essentially contains a mixture of meta- and ortho-xylene;
   a step for isomerization of C8 aromatics, in a catalytic unit (IS19) operating in the vapour phase and converting ethylbenzene, to treat the intermediate raffinate;
   a step for isomerization of C8 aromatics in a catalytic unit (IS20) operating in the liquid phase or in the vapour phase, to treat the 2-raffinate.

2. A process according to claim 1, further comprising, a step for purifying the para-xylene in at least a portion of the extract by crystallization.

3. A process according to claim 1, comprising at least the following steps:
   sending the feed (1) to a distillation column (CD2) from which a mixture (3) is extracted overhead comprising the major portion of the meta-xylene, para-xylene, ethylbenzene and at least a portion of the ortho-xylene, and from which a stream (4) of C9-C10 hydrocarbons and the remaining portion of the ortho-xylene are extracted from the bottom;
   separating the overhead mixture (3) in a simulated moving bed in at least one separation column (LM6) containing a plurality of interconnected beds and operating as a closed loop, said column comprising at least five zones defined by the injections of the stream (3) constituting the feed for the column (LM6) and the desorbant (5) and the withdrawals of said extract (7) containing para-xylene, said intermediate raffinate (8) containing ethylbenzene and said 2-raffinate (9) containing ortho-xylene and meta-xylene, the para-xylene desorption zone 1 being included between the desorbant injection (5) and the extract removal (7); the ethylbenzene, ortho-xylene and meta-xylene desorption zone 2 being included between the extract removal zone (7) and the adsorption feed injection (3); the para-xylene adsorption zone 3A being included between the feed injection (3) and the intermediate raffinate withdrawal (8); the ethylbenzene adsorption zone 3B being included between the intermediate fraction withdrawal (8) and the 2-raffinate withdrawal (9); and the zone 5 being included between the 2-raffinate withdrawal (9) and the desorbant injection (5);

distilling the intermediate raffinate (8) in a column (CD 11) to eliminate substantially all of the desorbant and withdrawing a first distilled fraction (14) containing ethyl benzene;

distilling the 2-raffinate in a column (CD 12) to eliminate substantially all of the desorbant and withdrawing a second distilled fraction (15);

distilling the extract (7) in a column (CD10) to recover a fraction (13) which is enriched in para-xylene;

sending said first distilled fraction (14) to a first zone for isomerizing C8 aromatics (IS19) operating in the vapour phase and converting ethylbenzene to obtain a first isomerate (22);

sending at least a portion of said second distilled fraction (15) to a second xylene isomerization zone (IS20) to obtain a second isomerate (21);

sending the first isomerate (22), after eliminating its light fractions, into a separation train (29) towards the distillation column (CD2);

recycling the second isomerate (21) either (stream 40) to the simulated moving bed separation column (LM6) as a mixture with the overhead stream (3) from the distillation column (CD2) or (stream 41) to the distillation column (CD2) as a mixture with the feed (1).

4. A process according to claim 3, in which the fraction (13) from the extract (7) is enriched in para-xylene with a purity of at least 50%, and is sent to at least one crystallization zone (CR23) to deliver para-xylene crystals and a mother liquor, the crystals being separated from the mother liquor, optionally taken up in suspension, washed and recovered (stream 24) and the mother liquor (25) is mixed with the feed (1) supplying the simulated moving bed separation column (LM6) via the column (CD2).

5. A process according to claim 1, in which a first isomerization zone (IS19) operating in the gas phase is operated under the following conditions:
a temperature of more than 300° C.;
a pressure of less than 4 MPa;
an hourly space velocity (HSV) of less than 10 h$^{-1}$;
a catalyst containing a zeolite with structure type EUO and at least one group VIII metal;
a H$_2$/hydrocarbon molar ratio of less than 10.

6. A process according to claim 1, in which a second isomerization zone (IS20) operating in the liquid phase is operated under the following conditions:
a temperature of less than 300° C.;
a pressure of less than 4 MPa;
an hourly space velocity (HSV) of less than 10 h$^{-1}$;
a catalyst containing a ZSM-5 type zeolite.

7. A process according to claim 1, in which the stream (4) from the bottom of the distillation column (CD2) is distilled in a distillation column (CD32) to produce an overhead stream (33) of high purity ortho-xylene, and a bottom stream (34) containing C9-C10 hydrocarbons.

8. A process according to claim 7, in which the stream containing ortho-xylene (33) is recycled to the isomerization zone in the liquid phase (IS20).

9. A process according to claim 1, in which the adsorbent used in the simulated moving bed separation unit (LM6) is a barium-enriched X zeolite or a potassium-enriched Y zeolite or a barium- and potassium-enriched Y zeolite.

10. A process according to claim 1, in which the desorbant used in the simulated moving bed separation unit (LM6) is selected from para-diethylbenzene, toluene, para-difluorobenzene or a mixture of diethylbenzenes.

11. A process according to claim 1, in which the volume ratio of the desorbant to the feed in the simulated moving bed separation unit (LM6) is in the range 0.5 to 2.5.

12. A process according to claim 1, in which the simulated moving bed separation unit (LM6) is operated at a temperature in the range 20° C. to 250° C. and at a pressure in the range from the bubble point of xylenes at the operating temperature to 2 MPa.

13. A process according to claim 3, in which the ethylbenzene content of the second distilled fraction from the 2-raffinate (stream 15) is at most 5% by weight.

14. A process according to claim 1, in which the gas phase isomerization unit (IS19) comprises a zeolite with structure type EUO and at least one metal from group VIII of the periodic table in a proportion of 0.01% to 2% by weight with respect to the catalyst.

15. A process according to claim 1, in which the catalyst from the gas vapour phase isomerization unit (IS19) contains an Eli-1 zeolite and platinum.

16. A process according to claim 3, in which a portion of the distilled stream from the 2-raffinate (stream 15) is sent to a set of units which can produce high purity meta-xylene and/or ortho-xylene.

17. Conducting a process according to claim 1, in the context of a modification to an existing unit with a view to increasing the quantity of para-xylene produced.

* * * * *

UNITED STATES PATENT AND TRADEMARK OFFICE
CERTIFICATE OF CORRECTION

| | |
|---|---|
| PATENT NO. | : 7,915,471 B2 |
| APPLICATION NO. | : 10/580345 |
| DATED | : March 29, 2011 |
| INVENTOR(S) | : Leflaive et al. |

It is certified that error appears in the above-identified patent and that said Letters Patent is hereby corrected as shown below:

Column 12, line 62 reads "separating the overhead mixture (3) in a simulated moving"

should read --separating the overhead mixture (3) in said simulated moving--.

Column 14, line 45 reads "from the gas vapour phase isomerization unit (IS19) contains"

should read --from the vapour phase isomerization unit (IS19) contains--.

Signed and Sealed this
Thirteenth Day of March, 2012

David J. Kappos
*Director of the United States Patent and Trademark Office*